United States Patent
Friedman et al.

(10) Patent No.: US 8,394,023 B2
(45) Date of Patent: Mar. 12, 2013

(54) METHOD AND APPARATUS FOR AUTOMATICALLY DETERMINING TIME TO AORTIC VALVE CLOSURE

(75) Inventors: Zvi M. Friedman, Kiriat Bialik (IL); Peter Lysyansky, Haifa (IL); Nahum Smirin, Haifa (IL)

(73) Assignee: General Electric Company, Schenectady, NY (US)

( * ) Notice: Subject to any disclaimer, the term of this patent is extended or adjusted under 35 U.S.C. 154(b) by 1307 days.

(21) Appl. No.: 12/119,390

(22) Filed: May 12, 2008

(65) Prior Publication Data

US 2009/0281424 A1 Nov. 12, 2009

(51) Int. Cl.
*A61B 8/00* (2006.01)
(52) U.S. Cl. ......... 600/437; 600/438; 600/450; 600/453
(58) Field of Classification Search ............. 600/407, 600/438–461
See application file for complete search history.

(56) References Cited

U.S. PATENT DOCUMENTS

| | | | |
|---|---|---|---|
| 5,139,020 A * | 8/1992 | Koestner et al. | 607/24 |
| 6,099,471 A * | 8/2000 | Torp et al. | 600/438 |
| 2004/0254486 A1 * | 12/2004 | Heimdal | 600/513 |
| 2006/0004291 A1 * | 1/2006 | Heimdal et al. | 600/459 |
| 2006/0058673 A1 * | 3/2006 | Aase et al. | 600/450 |
| 2007/0258631 A1 | 11/2007 | Friedman et al. | |

* cited by examiner

*Primary Examiner* — Elmer Chao
(74) *Attorney, Agent, or Firm* — The Small Patent Law Group; Dean D. Small (57) ABSTRACT

A method for determining a time to aortic valve closure comprises receiving data corresponding to an imaged region of a left ventricle of a heart. A plurality of points within the data is identified. A peak negative strain is determined for each of the points and the peak negative strain comprises a maximum contraction value and a time from onset to maximum contraction value. A weight value for each of the points is determined based on the peak negative strain. A time to aortic valve closure is determined based on the weight value and the time from onset to maximum contraction value for each of the points.

21 Claims, 9 Drawing Sheets

METHOD AND APPARATUS FOR AUTOMATICALLY DETERMINING TIME TO AORTIC VALVE CLOSURE

BACKGROUND OF THE INVENTION

This invention relates generally to medical imaging systems, and more particularly, to determining the time from onset to aortic valve closure using cardiac imaging.

Diagnosis of wall motion abnormality of the left ventricle may be performed using parametric imaging. One parameter that may be used is peak systolic strain (PSS), which is defined as the peak negative strain during systole. Determining the PSS requires knowing the timing of end-systole, or in other words, the timing of the aortic valve closure.

Aortic valve closure is a cardiac event that is relatively difficult to determine using gray-scale imaging. There are several methods that have been used that require operator expertise and interaction. One method has the operator position a Doppler curser to detect blood flow through the aortic valve. When no flow is present, the aortic valve is closed. However, the flow measurement is usually not simultaneous with the 2D measurements on which the strain analysis is based, and the heart rate between the measurements can vary to the extent that the aortic valve closure that is measured is not relevant for the strain based parametric imaging being used. Another method has the operator view the aortic valve on a monitor, such as in an apical long axis view (APLAX). The time of closure of the aortic valve is then determined by viewing the leaflets of the valve and identifying the correct frame of data. Unfortunately, the leaflets, as well as the aortic valve itself, are often difficult to view. These methods may be time consuming and may not result in the desired information.

Therefore, a need exists for minimizing the operator time and expertise needed when determining the time to aortic valve closure.

BRIEF DESCRIPTION OF THE INVENTION

In one embodiment, a method for determining a time to aortic valve closure comprises receiving data corresponding to an imaged region of a left ventricle of a heart. A plurality of points within the data is identified. A peak negative strain is determined for each of the points and the peak negative strain comprises a maximum contraction value and a time from onset to maximum contraction value. A weight value for each of the points is determined based on the peak negative strain. A time to aortic valve closure is determined based on the weight value and the time from onset to maximum contraction value for each of the points.

In another embodiment, a system for determining a time to aortic valve closure comprises a processor module configured to receive data corresponding to an imaged region of a left ventricle of a heart. The processor module is configured to determine peak negative strain for a plurality of points within the left ventricle. The peak negative strain comprises a maximum contraction value and a time from onset to maximum contraction value. The processor module is further configured to determine a weight value for each of the points based on the maximum contraction values and the time from onset to maximum contraction values. The processor module is further configured to determine a time to aortic valve closure based on the weight values and the time from onset to maximum contraction values. A display displays the time to aortic valve closure.

In yet another embodiment, a computer readable medium for determining a time to aortic valve closure comprises instructions to determine strain values based on data corresponding to a plurality of segments in an imaged region of the left ventricle of a heart. The computer readable medium also comprises instructions to determine an average peak negative strain for each of the segments, the average peak negative strain comprising a maximum contraction value and a time from onset to maximum contraction value. The computer readable medium further comprises instructions to determine a weight value for each of the average peak negative strains and instructions to determine a time to aortic valve closure based on the weight values and the time from onset to maximum contraction values.

DETAILED DESCRIPTION OF THE INVENTION

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

It should be noted that although the various embodiments may be described in connection with an ultrasound system, the methods and systems described herein are not limited to ultrasound imaging. In particular, the various embodiments may be implemented in connection with different types of medical imaging, including, for example, magnetic resonance imaging (MRI) and computed-tomography (CT) imaging. Further, the various embodiments may be implemented in other non-medical imaging systems, for example, non-destructive testing systems.

Exemplary embodiments of ultrasound systems and methods for calculating information are described in detail below. In particular, a detailed description of an exemplary ultrasound system will first be provided followed by a detailed description of various embodiments of methods and systems for automatically calculating time from onset to aortic valve closure (AVC). A technical effect of the various embodiments of the systems and methods described herein include at least one of automatically determining the time to AVC based on multiple strain traces and determining an estimate of error associated with the automatically determined data.

Figure 1:
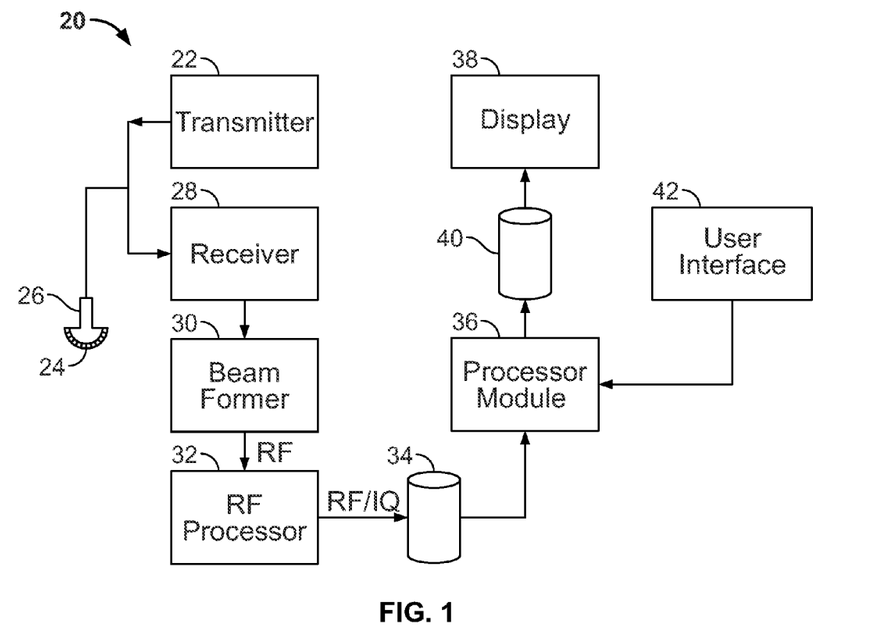
FIG. 1 illustrates a block diagram of an ultrasound system formed in accordance with an embodiment of the present invention.

FIG. 1 illustrates a block diagram of an ultrasound system 20. The ultrasound system 20 includes a transmitter 22 that drives an array of elements 24 (e.g., piezoelectric crystals) within a transducer 26 to emit pulsed ultrasonic signals into a body or volume. A variety of geometries may be used and the transducer 26 may be provided as part of, for example, different types of ultrasound probes. The ultrasonic signals are back-scattered from structures in the body, for example, blood cells or muscular tissue, to produce echoes that return to the elements 24. The echoes are received by a receiver 28. The received echoes are provided to a beamformer 30 that performs beamforming and outputs an RF signal. The RF signal is then provided to an RF processor 32 that processes the RF signal. Alternatively, the RF processor 32 may include a complex demodulator (not shown) that demodulates the RF signal to form IQ data pairs representative of the echo signals. The RF or IQ signal data may then be provided directly to a memory 34 for storage (e.g., temporary storage).

The ultrasound system 20 also includes a processor module 36 to process the acquired ultrasound information (e.g., RF signal data or IQ data pairs) and prepare frames of ultrasound information for display on a display 38. The processor module 36 is adapted to perform one or more processing operations according to a plurality of selectable ultrasound modalities on the acquired ultrasound information. Acquired ultrasound information may be processed in real-time during a scanning session as the echo signals are received. Additionally or alternatively, the ultrasound information may be stored temporarily in the memory 34 during a scanning session and processed in less than real-time in a live or off-line operation. An image memory 40 is included for storing processed frames of acquired ultrasound information that are not scheduled to be displayed immediately. The image memory 40 may comprise any known data storage medium, for example, a permanent storage medium, removable storage medium, etc.

The processor module 36 is connected to a user interface 42 that controls operation of the processor module 36 as explained below in more detail and is configured to receive inputs from an operator. The display 38 includes one or more monitors that present patient information, including diagnostic ultrasound images to the user for review, diagnosis and analysis. The display 38 may automatically display, for example, multiple planes from a three-dimensional (3D) ultrasound data set stored in the memory 34 or 40. One or both of the memory 34 and the memory 40 may store 3D data sets of the ultrasound data, where such 3D data sets are accessed to present 2D and 3D images. For example, a 3D ultrasound data set may be mapped into the corresponding memory 34 or 40, as well as one or more reference planes. The processing of the data, including the data sets, is based in part on user inputs, for example, user selections received at the user interface 42.

In operation, the system 20 acquires data, for example, volumetric data sets by various techniques (e.g., 3D scanning, real-time 3D imaging, volume scanning, 2D scanning with transducers having positioning sensors, freehand scanning using a voxel correlation technique, scanning using 2D or matrix array transducers, etc.). The data may be acquired by moving the transducer 26, such as along a linear or arcuate path, while scanning a region of interest (ROI). At each linear or arcuate position, the transducer 26 obtains scan planes that are stored in the memory 34.

Figure 2:
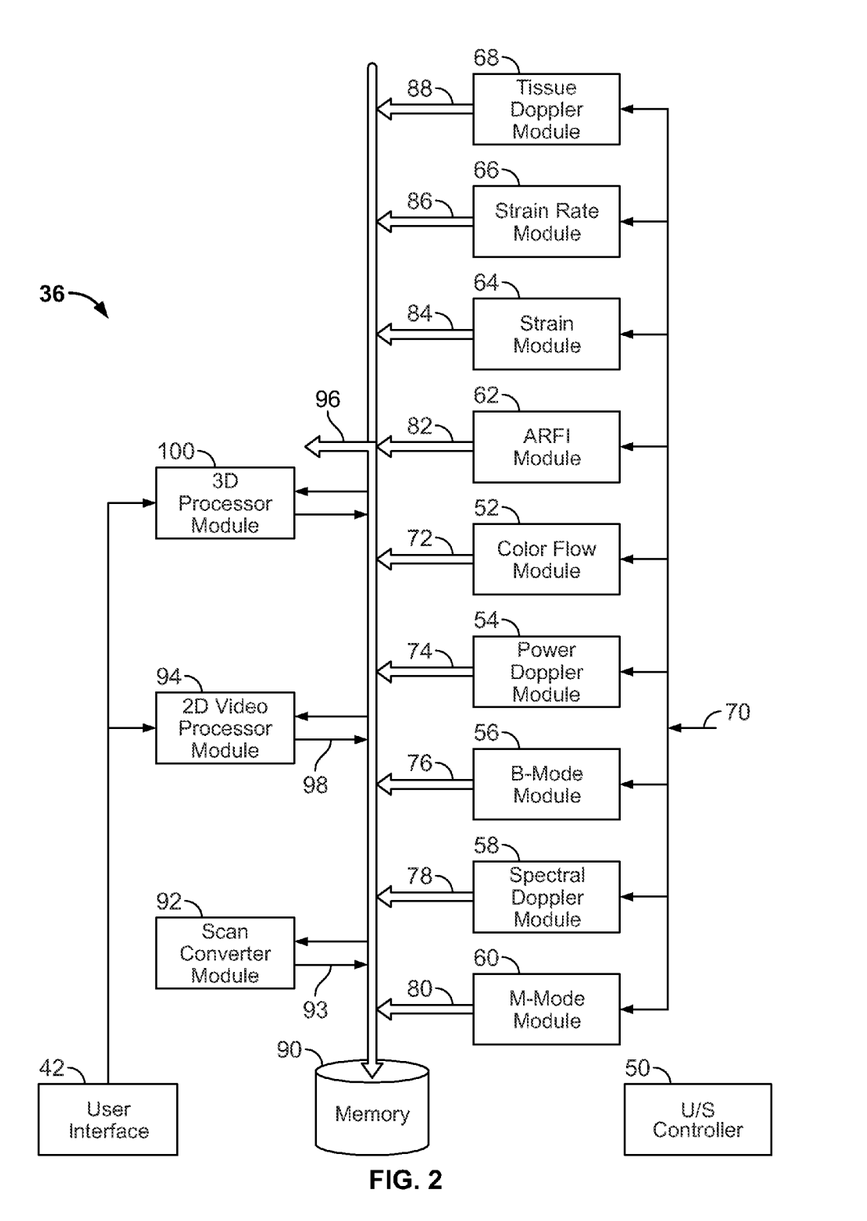
FIG. 2 illustrates an exemplary block diagram of the ultrasound processor module of FIG. 1 formed in accordance with an embodiment of the present invention.

FIG. 2 illustrates an exemplary block diagram of the ultrasound processor module 36 of FIG. 1. The ultrasound processor module 36 is illustrated conceptually as a collection of sub-modules, but may be implemented utilizing any combination of dedicated hardware boards, DSPs, processors, etc. Alternatively, the sub-modules of FIG. 2 may be implemented utilizing an off-the-shelf PC with a single processor or multiple processors, with the functional operations distributed between the processors. As a further option, the sub-modules of FIG. 2 may be implemented utilizing a hybrid configuration in which certain modular functions are performed utilizing dedicated hardware, while the remaining modular functions are performed utilizing an off-the-shelf PC and the like. The sub-modules also may be implemented as software modules within a processing unit.

The operations of the sub-modules illustrated in FIG. 2 may be controlled by a local ultrasound controller 50 or by the processor module 36. The sub-modules 52-68 perform mid-processor operations. The ultrasound processor module 36 may receive ultrasound data 70 in one of several forms. In the embodiment of FIG. 2, the received ultrasound data 70 constitutes IQ data pairs representing the real and imaginary components associated with each data sample. The IQ data pairs are provided to one or more of a color-flow sub-module 52, a power Doppler sub-module 54, a B-mode sub-module 56, a spectral Doppler sub-module 58 and an M-mode sub-module 60. Other sub-modules may be included such as an Acoustic Radiation Force Impulse (ARFI) sub-module 62, a strain sub-module 64, a strain rate sub-module 66, a Tissue Doppler (TDE) sub-module 68, among others. The strain sub-module 64, strain rate sub-module 66 and TDE sub-module 68 together may define an echocardiographic processing portion.

Each of sub-modules 52-68 are configured to process the IQ data pairs in a corresponding manner to generate color-flow data 72, power Doppler data 74, B-mode data 76, spectral Doppler data 78, M-mode data 80, ARFI data 82, echocardiographic strain data 84, echocardiographic strain rate data 86 and tissue Doppler data 88, all of which may be stored in a memory 90 (or memory 34 or image memory 40 shown in FIG. 1) temporarily before subsequent processing. The data 72-88 may be stored, for example, as sets of vector data values, where each set defines an individual ultrasound image frame. The vector data values are generally organized based on the polar coordinate system.

A scan converter sub-module 92 accesses and obtains from the memory 90 the vector data values associated with an image frame and converts the set of vector data values to Cartesian coordinates to generate an ultrasound image frame 93 formatted for display. The ultrasound image frames 93 generated by the scan converter sub-module 92 may be provided back to the memory 90 for subsequent processing or may be provided to the memory 34 or the image memory 40.

Once the scan converter sub-module 92 generates the ultrasound image frames 93 associated with, for example, the strain data 84, strain rate data 86, and the like, the image frames may be restored in the memory 90 or communicated over a bus 96 to a database (not shown), the memory 34, the image memory 40 and/or to other processors (not shown).

As an example, it may be desired to view different ultrasound images relating to echocardiographic functions in real-time on the display 38 (shown in FIG. 1). To do so, the scan converter sub-module 92 obtains strain or strain rate vector data sets for images stored in the memory 90. The vector data is interpolated where necessary and converted into an X,Y format for video display to produce ultrasound image frames. The scan converted ultrasound image frames are provided to a display controller (not shown) that may include a video processor that maps the video to a gray-scale mapping for video display. The gray-scale map may represent a transfer function of the raw image data to displayed gray levels. Once the video data is mapped to the gray-scale values, the display controller controls the display 38, which may include one or more monitors or windows of the display, to display the image frame. The echocardiographic image displayed in the display 38 is produced from an image frame of data in which each datum indicates the intensity or brightness of a respective pixel in the display. In this example, the display image represents muscle motion in a region of interest being imaged.

Referring again to FIG. 2, a 2D video processor sub-module 94 may be used to combine one or more of the frames generated from the different types of ultrasound information. For example, the 2D video processor sub-module 94 may combine different image frames by mapping one type of data to a gray map and mapping the other type of data to a color map for video display. In the final displayed image, the color pixel data is superimposed on the gray scale pixel data to form a single multi-mode image frame 98 that is again re-stored in the memory 90 or communicated over the bus 96. Successive frames of images may be stored as a cine loop in the memory 90 or memory 40 (shown in FIG. 1). The cine loop represents a first in, first out circular image buffer to capture image data that is displayed in real-time to the user, such as one or more heart cycles. The user may freeze the cine loop by entering a freeze command at the user interface 42. The user interface 42 may include, for example, a keyboard and mouse and all other input controls associated with inputting information into the ultrasound system 20 (shown in FIG. 1).

A 3D processor sub-module 100 is also controlled by the user interface 42 and accesses the memory 90 to obtain spatially consecutive groups of ultrasound image frames and to generate three dimensional image representations thereof, such as through volume rendering or surface rendering algorithms as are known. The three dimensional images may be generated utilizing various imaging techniques, such as ray-casting, maximum intensity pixel projection and the like.

Figure 3:
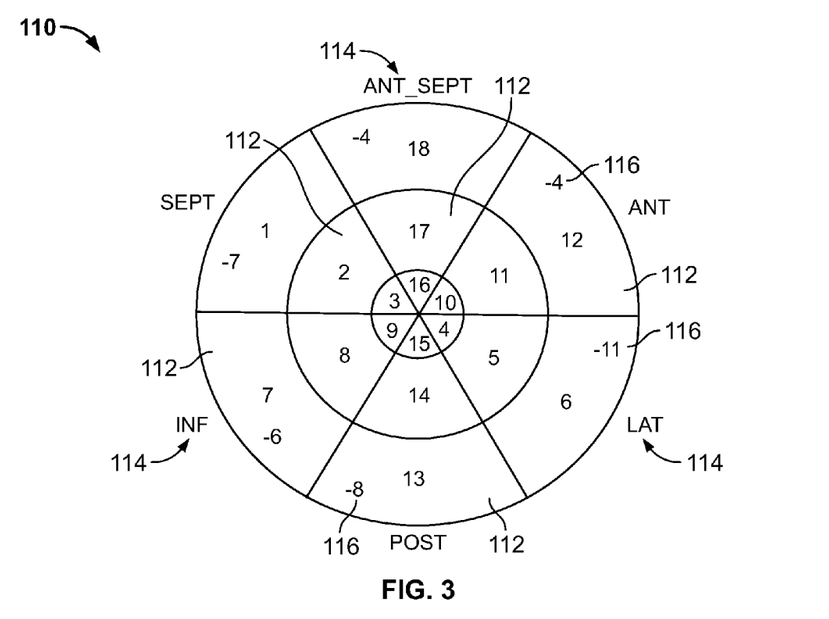
FIG. 3 illustrates a segmented display representing the left ventricle that may be configured in a bullseye arrangement in accordance with an embodiment of the present invention.
Figure 4:
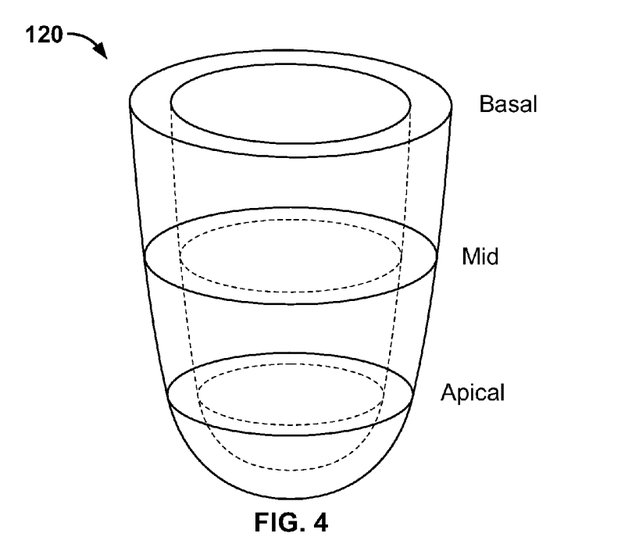
FIG. 4 illustrates a segmented model of a heart in accordance with an embodiment of the present invention.

Various embodiments of the present invention calculate a time to AVC from measured cardiac activity. An indication of the reliability of the time to AVC may also be provided. The time to AVC may be calculated based on data detected within the left ventricle (LV). For example, a segmented display 110 of the LV is shown in FIG. 3 and may be configured in a bullseye arrangement. The segmented display 110 generally includes a plurality of segments 112 forming segmented areas or regions and together defining a circular display that may be configured as a parametric display of the entire myocardial surface of a heart. The parametric display may be generated in any known manner, for example, by interpolation of peak systolic values along a myocardial wall of a heart acquired and processed in different views, such as three standard apical views (apical long axis (APLAX), four chamber and two chamber). It should be noted that the segmented display 110 may be modified to include a different number of segments 112, for example, seventeen or sixteen segments. The number of segments 112 generally may be more than or less than the eighteen segments shown and may be based on a segmented model 120 of a heart, for example, as shown in FIG. 4.

Position labels 114 indicate the location/orientation from which strain information was acquired (e.g., posterior (POST), anterior (ANT), etc.) based on the segmented model 120. The position labels 114 are generally associated with a different slice of the segmented display. The order of the segments 112 are numerically identified in FIG. 3, for example, using any known or conventional/standard numbering and ordering, for example, with the segments 112 numbered and representing various heart segments (e.g., apical, mid and basal) along the corresponding wall (e.g., septal (SEPT), lateral (LAT), anterior, posterior, etc.). However, the arrangement, positioning and ordering of the segments 112 may be modified as desired or needed.

In general, the segmented display 110 displays quantitative parameters derived from measured strain of cardiac activity. For example, each of the segments 112 may be numerically and/or graphically labeled to show the corresponding strain derived parameters. In one embodiment, the parameter is average peak negative strain 116 (illustrated in a portion of the segments 112), which may also be known as average peak systolic strain. The calculated strain measured from tissue deformation may be determined using strain traces or any other known manner, for example, by determining a velocity field for each segmented region based on tracking structures in the heart from one image frame to the next. Local velocities may be determined, for example, from maps of the frames.

The segmented display 110 may be presented on a screen or a portion thereof (e.g., a window) of the display 38 (shown in FIG. 1). In one embodiment, the calculated average peak negative strain 116 may be displayed within each segment 112. In another embodiment, an indication of reliability (not shown) may correspond with one or more of the segments 112. The indication of reliability may be based on a standard deviation of the strain traces within the segment 112, and may be displayed as a particular color, pattern, in a graph or table, and the like.

In addition to standard deviation, it may be determined that strain values include errors or that insufficient information exists to acquire accurate measurements resulting in possibly unreliable data, such as having tracking information below a predetermined level, for example, below an acceptable or poor tracking level. This determination may be based on any of a plurality of factors, including, for example, image quality, image noise, etc. The segments 112 having calculated strain values that are based on acquired data that is below the predetermined level may be marked or indicated accordingly.

Figure 5:
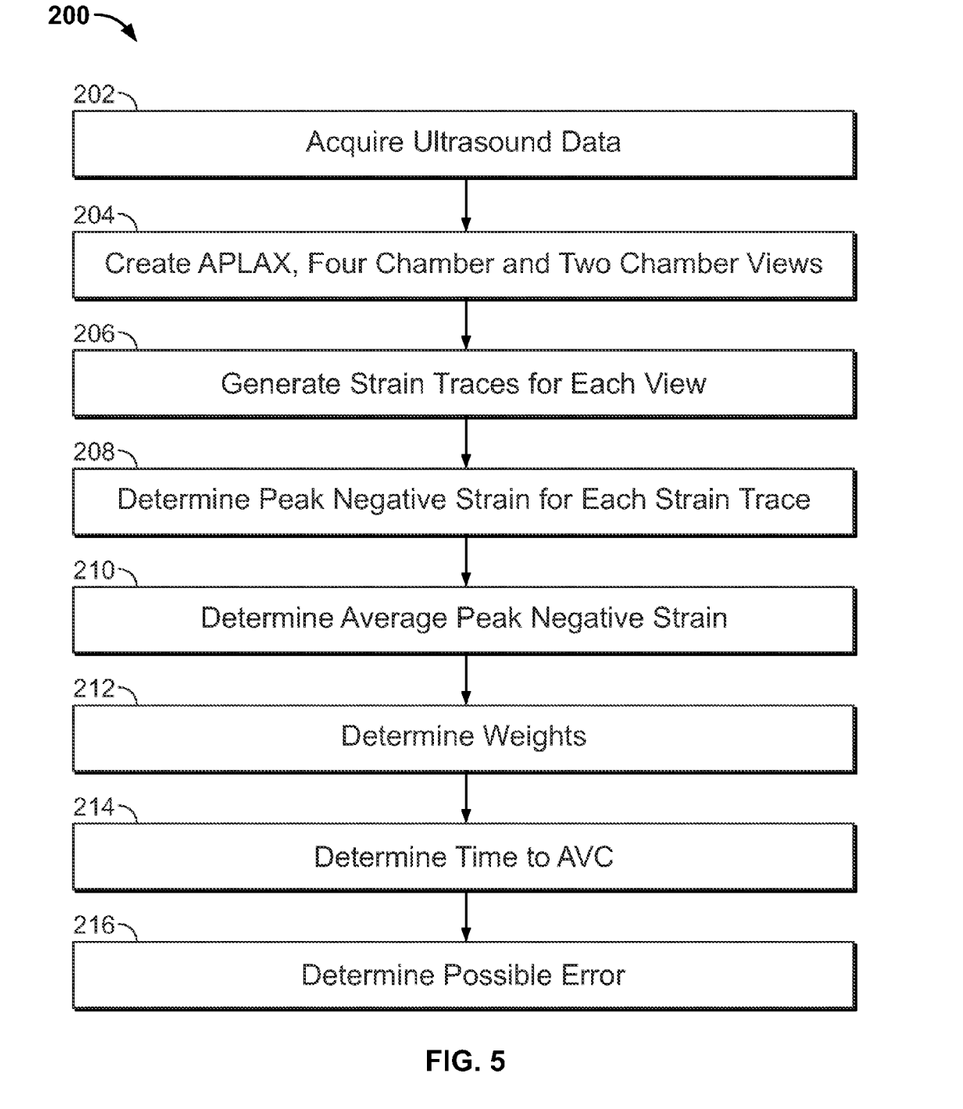
FIG. 5 illustrates a method for automatically calculating the time to aortic valve closure (AVC) in accordance with an embodiment of the present invention.

FIG. 5 illustrates a method 200 for automatically calculating the time to AVC. As discussed previously, it may be difficult and time consuming to manually determine the time to AVC. In a well synchronized heart, all of the segments 112 (or areas within the LV) achieve maximum contraction at the same, or nearly the same, time within the cardiac cycle. The time of maximum contraction is the time of AVC. However, in a poorly synchronized heart, some segments 112 may contract with a delay and may experience a decreased level or amount of contraction. In other words, the segments 112 are not all contracting at the same time and the stronger segments 112 contract quicker and to a higher degree than weaker segments 112.

Figure 6:
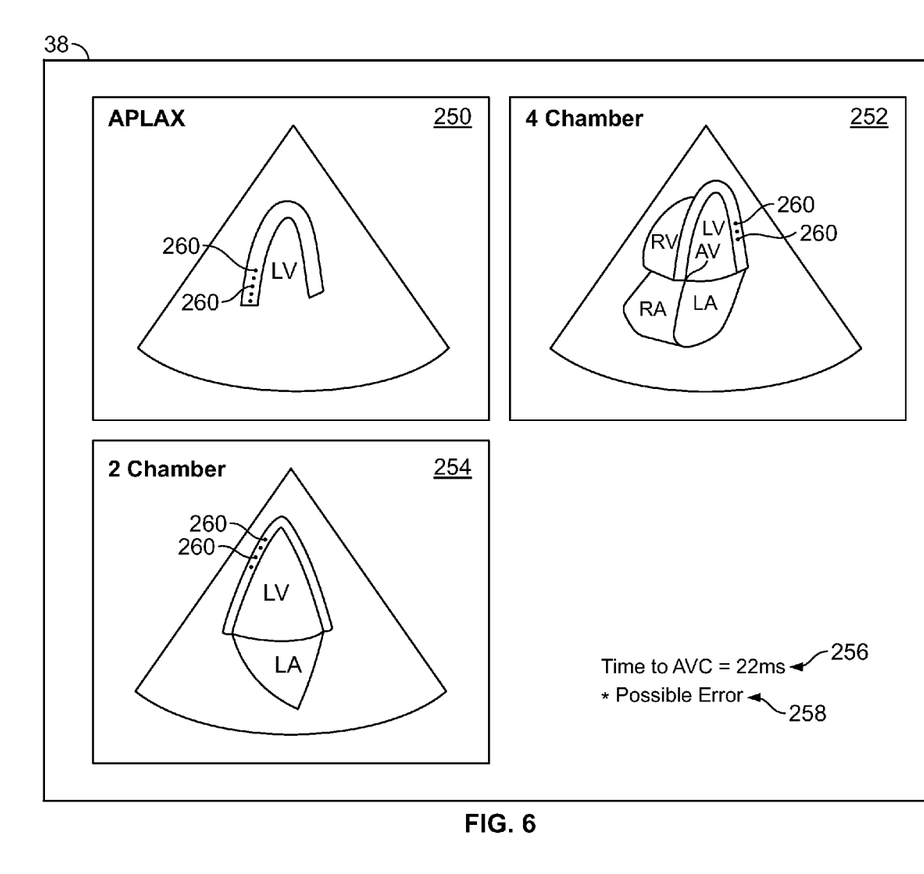
FIG. 6 illustrates three apical views that may be displayed on the display of FIG. 1 in accordance with an embodiment of the present invention.

At 202 of FIG. 5, ultrasound data is acquired, such as by using the system 20 of FIG. 1. The ultrasound data may be a volume of data over time, covering at least one heart cycle. In another embodiment, the data may be different diagnostic data, such as CT data. At 204, three standard apical views are created based on the ultrasound data. FIG. 6 illustrates three apical views that may be displayed on the display 38 of FIG. 1. An APLAX view 250, four chamber view 252 and two chamber view 254 are shown. Other views may be used, but it is desirable to create a set of views that includes all of the segments 112. In general, each of the views may have six segments 112 (not shown) that together form the segments 112 illustrate in FIG. 3. In another embodiment, the three apical views may be created and stored in memory 40 but may not be displayed on the display 38.

At 206, strain traces are generated for each of the APLAX, four chamber and two chamber views 250, 252 and 254, such as by the strain module 64 and the strain rate sub-module 66 (shown in FIG. 2) within the processor module 36. A strain trace is strain as a function of time and is calculated for multiple points 260 (shown in FIG. 6) within each view. It should be understood that only a small number of representative points 260 are shown. For example, points 260 may be identified in a segment 112, such as being positioned 2 millimeters (mm) apart, and tracked throughout the heart cycle. In one embodiment, forty-eight points 260 may be defined in each view wherein each of the six segments in a view has eight points 260. It should be understood that more or less points 260 may be defined and that the points 260 may be evenly or unevenly distributed between the views and between the segments within the views. In another embodiment, each point 260 may be tracked relative to a nearest neighbor point 260 over time to measure the change in distance there-between or the local contraction.

At 208, the processor module 36 may determine peak negative strain for each strain trace. Each peak negative strain includes a maximum contraction value and a time from onset to maximum contraction value. For example, local contraction of the tissue associated with the two points 260 over time is determined. The two points 260 are separated by an initial length L prior to onset. Contraction may be determined as a percentage of shortening. If the two points 260 are initially separated by a length L prior to the LV contraction, the local contraction associated with the points 260 may be determined as $\Delta L/L$, wherein $\Delta L$ is the change in L during the contraction. For example, if the initial length L is 2 mm, at a point in time during the heart cycle L may be 1.8 mm, and thus $\Delta L=0.2$. The local contraction may be determined, at that point in time, as $0.2/2 = -10$ percent. Therefore, the local contraction is determined over the heart cycle (e.g. multiple points in time) to identify the time from onset where the peak negative strain occurs.

At 210, in some embodiments the processor module 36 may determine the average peak negative strain based on multiple strain values. For example, the average peak negative strain may be determined for each segment 112 or for each view. The average peak negative strain includes values representative of the time to peak negative strain as well as the percent contraction (or amount of contraction). If computed for a segment 112, the average peak negative strain indicates an average time and amount of maximum contraction for the corresponding segment 112. It should be understood that the average peak negative strain may be calculated in different ways, such as averaging all strain traces within the segment 112 or view, or by calculating a mean. Also, some values may not be included in the calculation if the values are outside predetermined parameters. In another embodiment, a measured peak negative strain (such as from a point 260 within a segment 112) may be used rather than the calculated average peak negative strain.

At 212, the processor module 36 determines a weight (e.g. weight value). In one embodiment, a weight may be determined for each point 260 based on the associated peak negative strain. In another embodiment, a weight may be determined for each of the segments 112 or views based on the corresponding average peak negative strain. The weight value may be based on one or both of the amount of contraction and the time from onset to maximum contraction. For example, the following equation may be used:

$$\text{weight value} = \text{max contraction value}/(\text{time from onset to max contraction value}^4) \qquad \text{Eq. 1}$$

It should be understood that the weight value may be calculated based on a function other than Eq. 1 that uses the maximum contraction value and the time from onset to maximum contraction value. Also, other measurements may be used, additionally or to replace a value in Eq. 1 or a different function, such as strain, strain rate and time to peak strain. Continuing the example above, if the maximum contraction value or maximum strain was 0.2 and the time from onset to maximum contraction is 20 milliseconds (ms), the weight value may be calculated as $0.2/(20^4)$, or 0.00000125. If the maximum contraction value is 0.2 and the time from onset to maximum contraction is greater, such as 30 ms, the weight value would be less. Also, for equal times from onset to maximum contraction, the segment 112 or point 260 that has the greater percentage of contraction receives a greater weight value. Therefore, a first segment or point 260 having a relatively shorter time from onset to maximum contraction receives a relatively greater weight value compared to a second segment or point 260 having a relatively longer time from onset to maximum contraction, and a third segment or point 260 having a relatively larger maximum contraction value receives a relatively greater weight value compared to a fourth segment or point 260 having a relatively weaker maximum contraction value.

At 214, the processor module 36 determines the time to AVC, such as by computing a weighted average. For example, when determining using segments 112, a sum of the averaged time to peak negative strain values may be calculated and divided by the sum of the weights. When determining using points 260, a sum of the time to peak negative strain values may be calculated and divided by the sum of the weights. The processor module 36 may display time to AVC 256, such as on the display 38 of FIG. 6. Therefore, the time to AVC 256 may be automatically calculated and displayed by the system 20. Although not shown, the processor module 36 may also display one or more strain traces, such as by displaying an average strain trace corresponding to each of the segments 112. In addition, the processor module 36 may display the segmented display 110 (shown in FIG. 3), indicating with a number, color or pattern the time to AVC within each segment 112 (not shown).

At 216, the processor module 36 may determine an estimate or indication of possible error associated with the time to AVC. For example, a standard deviation may be calculated for each of the segments 112 based on the strain traces within the corresponding segment 112. If the standard deviation is beyond one or more preset parameters, the processor module 36 may display an error indication 258 on the display 38. In another embodiment, the error indication 258 may be displayed if a minimum number of segments 112, such as one, two or three segments 112, or a minimum number of points 260, have standard deviations beyond the preset parameters. In yet another embodiment, the error indication 258 may also indicate a percentage or degree of probable error. Also, if the error indication 258 is severe such that the time to AVC 256 is not considered to be valid, the time to AVC 256 may not be displayed. It should be understood that error calculations may be used other than standard deviation.

In other embodiments, a subset of the segments 112 or points 260 may be used to calculate the time to AVC. For example, the time to AVC may be computed based on the segments 112 or points 260 within two of the views, such as the APLAX view 250 and the four chamber view 252, or the APLAX view 250 and the two chamber view 254. In another embodiment, a segment 112 may be excluded from the calculation of the time to AVC based on a determination that poor, insufficient, or erroneous data associated with that segment 112 was received.

Figure 7:
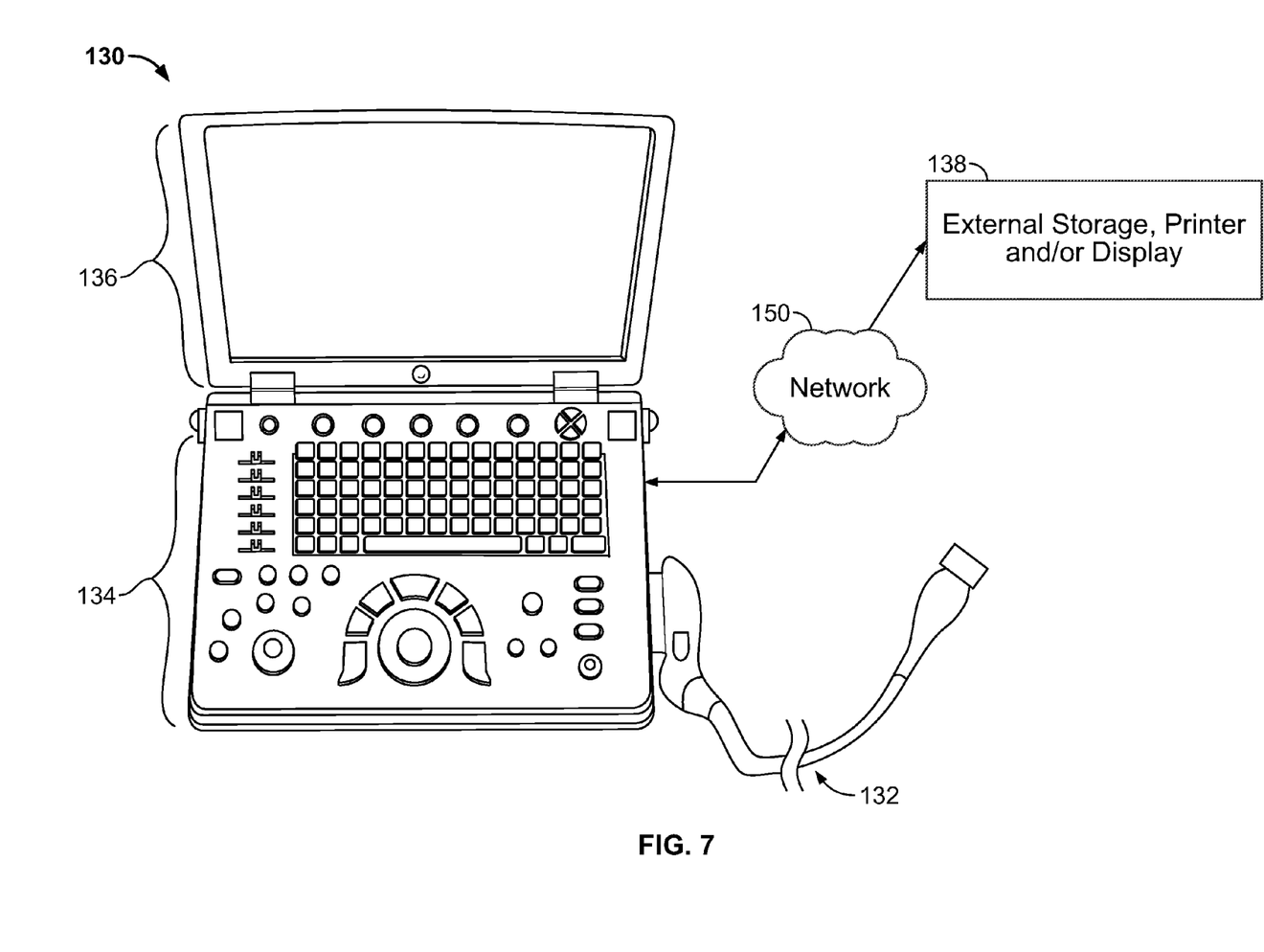
FIG. 7 illustrates a miniaturized ultrasound imaging system that may be configured to automatically calculate the time to AVC in accordance with an embodiment of the present invention.

FIG. 7 illustrates a 3D-capable miniaturized ultrasound imaging system 130 having a transducer 132 that may be configured to automatically calculate the time to AVC. For example, the transducer 132 may have a 2D array of transducer elements 104 as discussed previously with respect to the transducer 106 of FIG. 1. A user interface 134 (that may also include an integrated display 136) is provided to receive commands from an operator. As used herein, "miniaturized" means that the ultrasound system 130 is a handheld or hand-carried device or is configured to be carried in a person's hand, pocket, briefcase-sized case, or backpack. For example, the ultrasound system 130 may be a hand-carried device having a size of a typical laptop computer, for instance, having dimensions of approximately 2.5 inches in depth, approximately 14 inches in width, and approximately 12 inches in height. The ultrasound system 130 may weigh about ten pounds, and thus is easily portable by the operator. The integrated display 136 (e.g., an internal display) is also provided and is configured to display a medical image.

The ultrasonic data may be sent to an external device 138 via a wired or wireless network 150 (or direct connection, for example, via a serial or parallel cable or USB port). In some embodiments, external device 138 may be a computer or a workstation having a display. Alternatively, external device 138 may be a separate external display or a printer capable of receiving image data from the hand carried ultrasound system 130 and of displaying or printing images that may have greater resolution than the integrated display 136.

Figure 8:
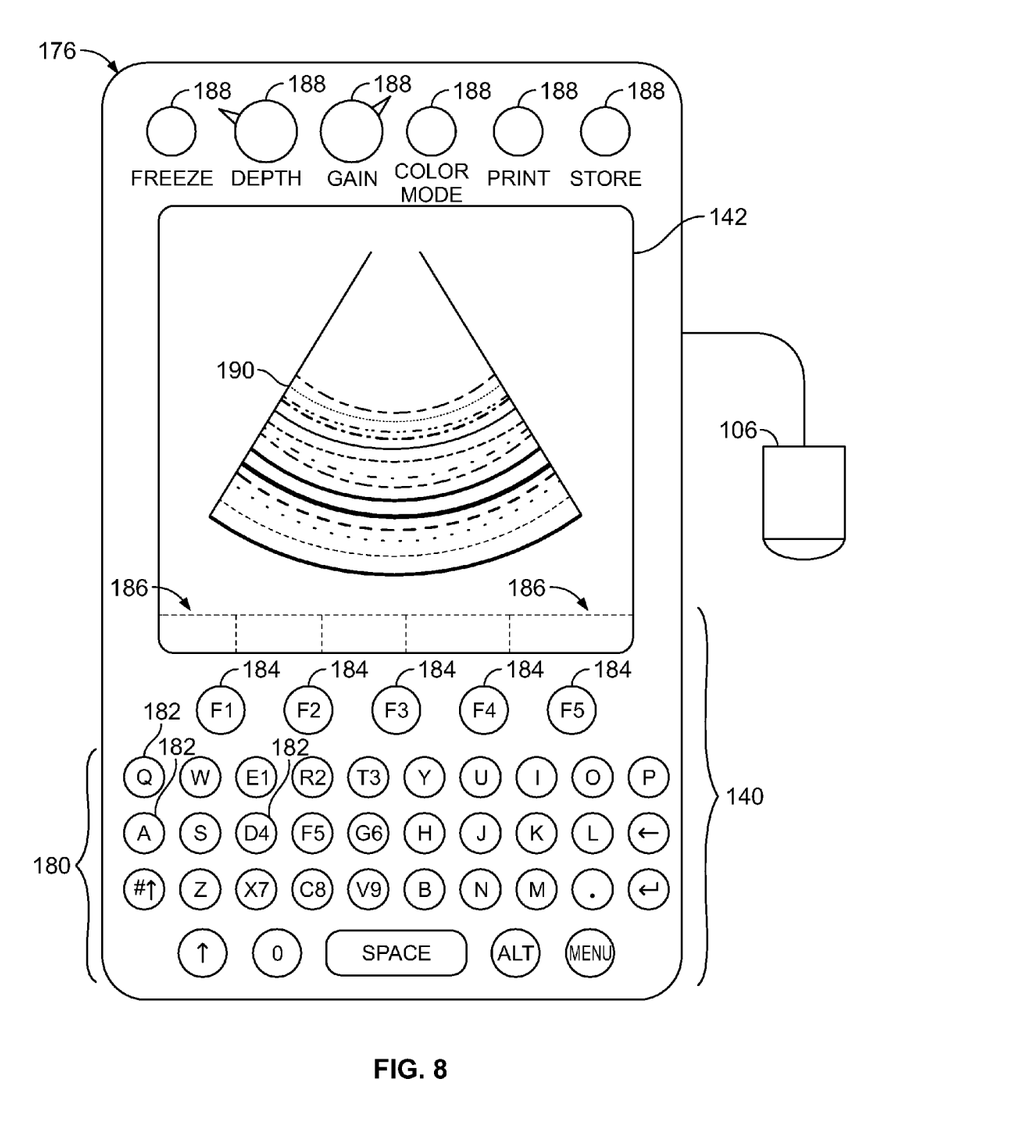
FIG. 8 illustrates a hand carried or pocket-sized ultrasound imaging system that may be configured to automatically calculate the time to AVC in accordance with an embodiment of the present invention.

FIG. 8 illustrates a hand carried or pocket-sized ultrasound imaging system 176 that may be configured to automatically calculate the time to AVC. In the system 176, display 142 and user interface 140 form a single unit. By way of example, the pocket-sized ultrasound imaging system 176 may be a pocket-sized or hand-sized ultrasound system approximately 2 inches wide, approximately 4 inches in length, and approximately 0.5 inches in depth and weighs less than 3 ounces. The display 142 may be, for example, a 320×320 pixel color LCD display (on which a medical image 190 may be displayed). A typewriter-like keyboard 180 of buttons 182 may optionally be included in the user interface 140. It should be noted that the various embodiments may be implemented in connection with a pocket-sized ultrasound system 176 having different dimensions, weights, and power consumption.

Multi-function controls 184 may each be assigned functions in accordance with the mode of system operation. Therefore, each of the multi-function controls 184 may be configured to provide a plurality of different actions. Label display areas 186 associated with the multi-function controls 184 may be included as necessary on the display 142. The system 176 may also have additional keys and/or controls 188 for special purpose functions, which may include, but are not limited to "freeze," "depth control," "gain control," "color-mode," "print," and "store."

Figure 9:
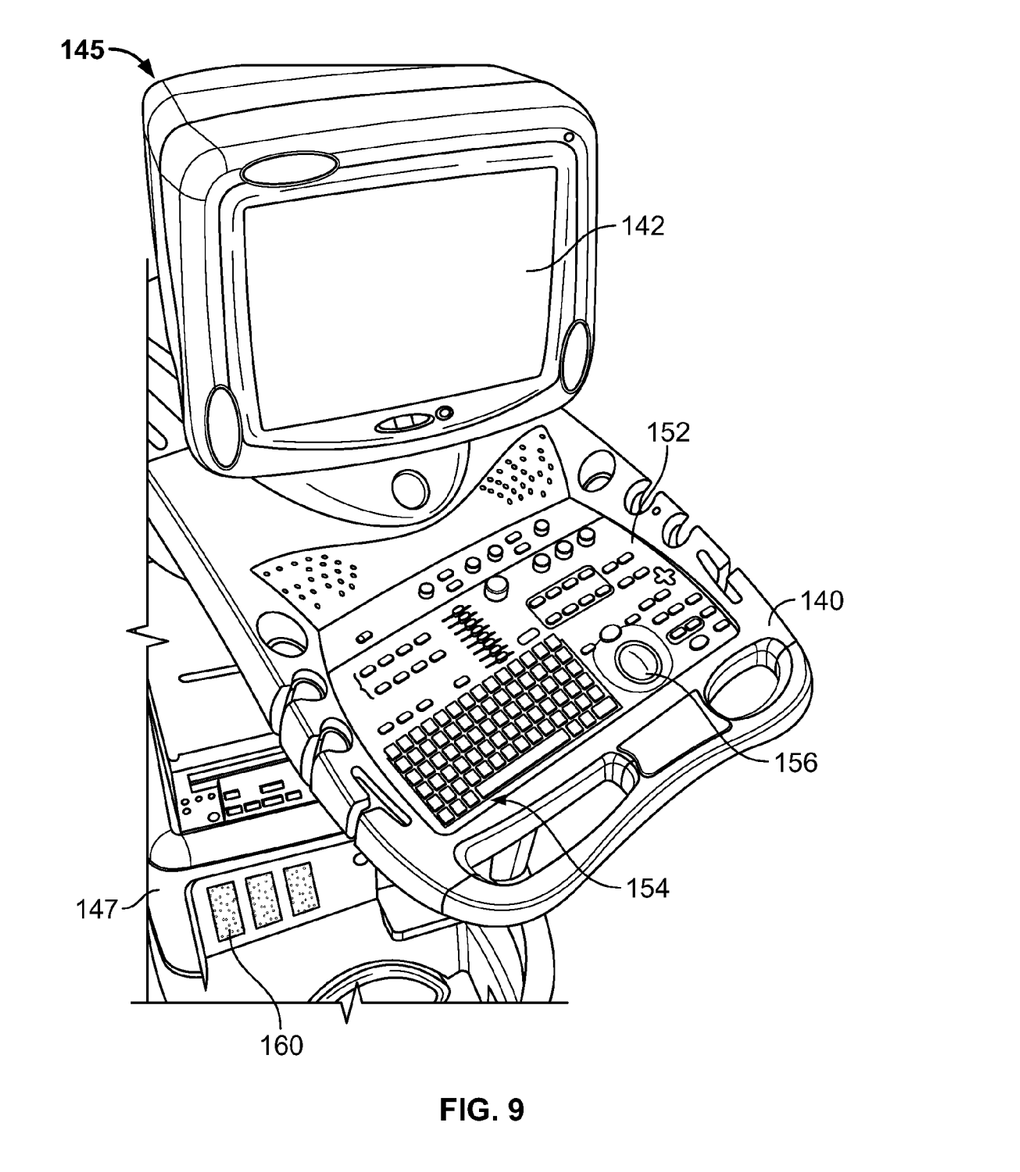
FIG. 9 illustrates a console-based ultrasound imaging system provided on a movable base that may be configured to automatically calculate the time to AVC in accordance with an embodiment of the present invention.

FIG. 9 illustrates a console-based ultrasound imaging system 145 provided on a movable base 147 that may be configured to automatically calculate the time to AVC. The portable ultrasound imaging system 145 may also be referred to as a cart-based system. A display 142 and user interface 140 are provided and it should be understood that the display 142 may be separate or separable from the user interface 140. The user interface 140 may optionally be a touchscreen, allowing the operator to select options by touching displayed graphics, icons, and the like.

The user interface 140 also includes control buttons 152 that may be used to control the portable ultrasound imaging system 145 as desired or needed, and/or as typically provided. The user interface 140 provides multiple interface options that the user may physically manipulate to interact with ultrasound data and other data that may be displayed, as well as to input information and set and change scanning parameters. The interface options may be used for specific inputs, programmable inputs, contextual inputs, and the like. For example, a keyboard 154 and track ball 156 may be provided. The system 145 has at least one probe port 160 for accepting probes.

Figure 10:
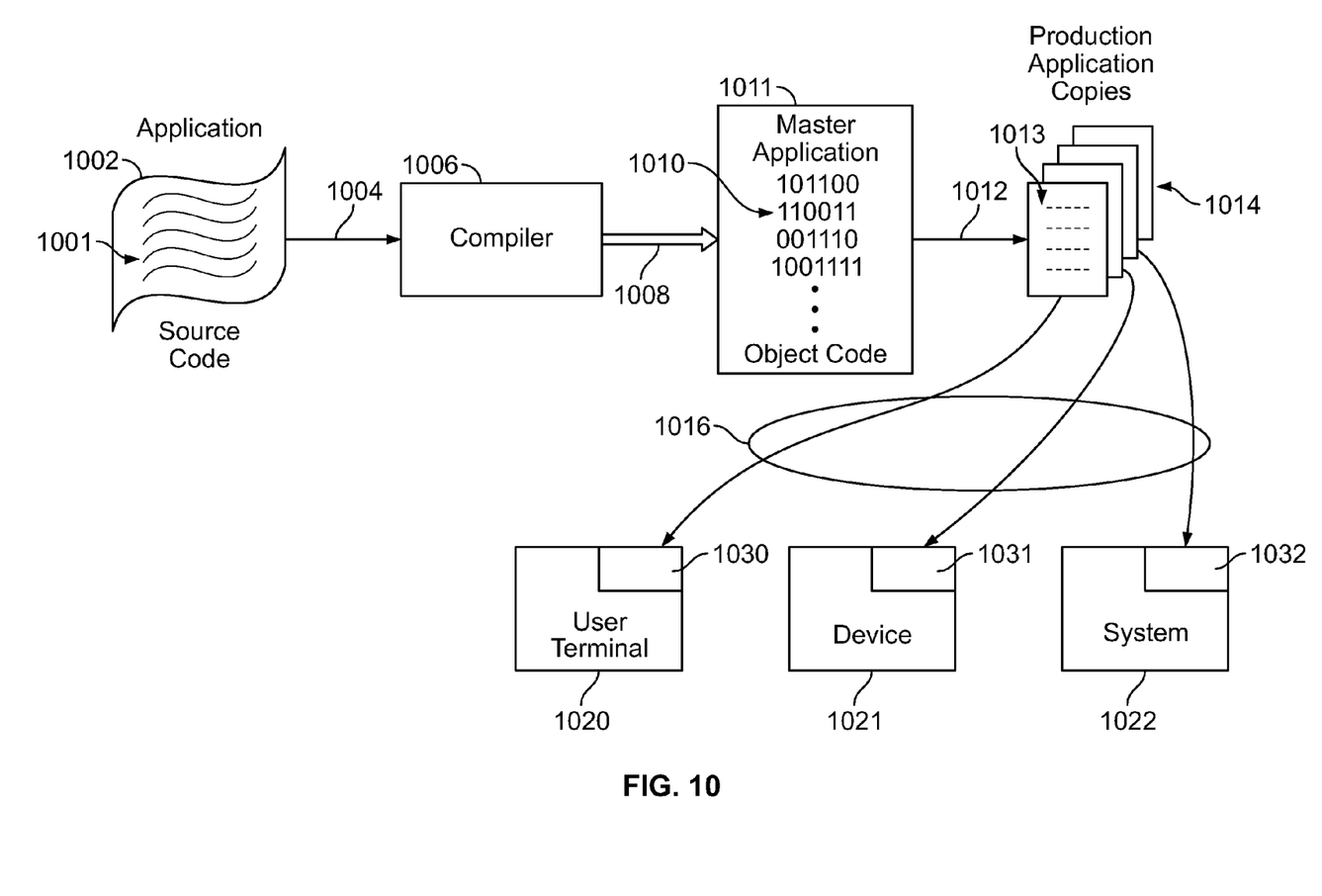
FIG. 10 illustrates a block diagram of exemplary manners in which embodiments of the present invention may be stored, distributed and installed on computer readable medium.

FIG. 10 illustrates a block diagram of exemplary manners in which embodiments of the present invention may be stored, distributed and installed on computer readable medium. In FIG. 10, the "application" represents one or more of the methods and process operations discussed above. For example, the application may represent the process carried out in connection with FIG. 5 as discussed above.

As shown in FIG. 10, the application is initially generated and stored as source code 1001 on a source computer readable medium 1002. The source code 1001 is then conveyed over path 1004 and processed by a compiler 1006 to produce object code 1010. The object code 1010 is conveyed over path 1008 and saved as one or more application masters on a master computer readable medium 1011. The object code 1010 is then copied numerous times, as denoted by path 1012, to produce production application copies 1013 that are saved on separate production computer readable medium 1014. The production computer readable medium 1014 is then conveyed, as denoted by path 1016, to various systems, devices, terminals and the like. In the example of FIG. 10, a user terminal 1020, a device 1021 and a system 1022 are shown as examples of hardware components, on which the production computer readable medium 1014 are installed as applications (as denoted by 1030-1032).

The source code may be written as scripts, or in any high-level or low-level language. Examples of the source, master, and production computer readable medium 1002, 1011 and 1014 include, but are not limited to, CDROM, RAM, ROM, Flash memory, RAID drives, memory on a computer system and the like. Examples of the paths 1004, 1008, 1012, and 1016 include, but are not limited to, network paths, the internet, Bluetooth, GSM, infrared wireless LANs, HIPERLAN, 3G, satellite, and the like. The paths 1004, 1008, 1012, and 1016 may also represent public or private carrier services that transport one or more physical copies of the source, master, or production computer readable medium 1002, 1011 or 1014 between two geographic locations. The paths 1004, 1008, 1012 and 1016 may represent threads carried out by one or more processors in parallel. For example, one computer may hold the source code 1001, compiler 1006 and object code 1010. Multiple computers may operate in parallel to produce the production application copies 1013. The paths 1004, 1008, 1012, and 1016 may be intra-state, inter-state, intra-country, inter-country, intra-continental, inter-continental and the like.

The operations noted in FIG. 10 may be performed in a widely distributed manner world-wide with only a portion thereof being performed in the United States. For example, the application source code 1001 may be written in the United States and saved on a source computer readable medium 1002 in the United States, but transported to another country (corresponding to path 1004) before compiling, copying and installation. Alternatively, the application source code 1001 may be written in or outside of the United States, compiled at a compiler 1006 located in the United States and saved on a master computer readable medium 1011 in the United States, but the object code 1010 transported to another country (corresponding to path 1012) before copying and installation. Alternatively, the application source code 1001 and object code 1010 may be produced in or outside of the United States, but production application copies 1013 produced in or conveyed to the United States (e.g. as part of a staging operation) before the production application copies 1013 are installed on user terminals 1020, devices 1021, and/or systems 1022 located in or outside the United States as applications 1030-1032.

As used throughout the specification and claims, the phrases "computer readable medium" and "instructions configured to" shall refer to any one or all of i) the source computer readable medium 1002 and source code 1001, ii) the master computer readable medium and object code 1010, iii) the production computer readable medium 1014 and production application copies 1013 and/or iv) the applications 1030-1032 saved in memory in the terminal 1020, device 1021 and system 1022.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for determining a time to aortic valve closure, comprising:
    receiving data corresponding to an imaged region of a left ventricle of a heart;
    identifying a plurality of points within the data;
    determining, using a processor, a peak negative strain for each of the points, the peak negative strain comprising a maximum contraction value and a time from onset to maximum contraction value;
    determining, using a processor, a weight value for each of the points based on the peak negative strain associated with the points; and
    determining, using the processor, a time to aortic valve closure based on the weight value and the time from onset to maximum contraction value for each of the points.

2. The method of claim 1, wherein the data corresponds to a plurality of segments, wherein an average peak negative strain is based on a plurality of strain values determined for the points within the corresponding segment, the time to aortic valve closure being further based on averaged time from onset to maximum contraction values.

3. The method of claim 1, wherein the data corresponds to a plurality of segments, the method further comprising:
    generating strain traces based on the points within each of the segments; and
    determining, using the processor, an average peak negative strain based on the strain traces, the time to aortic valve closure being further based on averaged time from onset to maximum contraction values.

4. The method of claim 1, the determining the time to aortic valve closure further comprising computing a weighted average.

5. The method of claim 1, wherein the determining a weight value further comprises dividing the maximum contraction value by the time from onset to maximum contraction value to a power of four.

6. The method of claim 1, wherein the determining a weight value further comprises applying a greater weight value to the peak negative strain of a first point that has a relatively shorter time from onset to maximum contraction value compared to a second point that has a relatively longer time from onset to maximum contraction value.

7. The method of claim 1, wherein the determining a weight value further comprises applying a greater weight value to the average peak negative strain of a first point that has a relatively greater maximum contraction value compared to a second point that has a relatively weaker maximum contraction value.

8. The method of claim 1, wherein the data is based on at least two ultrasonic views of the left ventricle, the ultrasonic views being an apical long axis view, a four chamber view and a two chamber view.

9. The method of claim 1, wherein the data corresponds to a plurality of segments, the method further comprising:
  determining, using the processor, an average peak negative strain for the segments based on the points within the associated segment, the time to aortic valve closure being further based on averaged time from onset to maximum contraction values;
  determining, using the processor, a standard deviation based on the average peak negative strain; and
  indicating an estimate of error associated with the time to aortic valve closure based on the standard deviation.

10. The method of claim 1, wherein determining the time to aortic valve closure further comprises dividing a sum of the time from onset to maximum contraction value of the points by a sum of the weight values of the points.

11. A system for determining a time to aortic valve closure, comprising:
  a processor module configured to receive data corresponding to an imaged region of a left ventricle of a heart, the processor module configured to determine peak negative strain for a plurality of points within the left ventricle, the peak negative strain comprising a maximum contraction value and a time from onset to maximum contraction value, the processor module further configured to determine a weight value for each of the points based on the maximum contraction values and the time from onset to maximum contraction values associated with the points, the processor module further configured to determine a time to aortic valve closure based on the weight values and the time from onset to maximum contraction values; and
  a display for displaying the time to aortic valve closure.

12. The system of claim 11, wherein the processor module is configured to receive the data as data that is based on ultrasonic views of the left ventricle, the views being an apical long axis view, a four chamber view and a two chamber view.

13. The system of claim 11, wherein the processor module is configured to receive the data as data that corresponds to a plurality of segments, the processor module further configured to calculate an average peak negative strain based on a plurality of strain values associated with the points within the corresponding segment, the processor module further configured to determine the time to aortic valve closure based on averaged time from onset to maximum contraction values.

14. The system of claim 11, wherein the processor module is configured to receive the data as data that corresponds to a plurality of segments, wherein each of the segments has at least one of the points there-within, the processor module further configured to determine strain values associated with the points, the processor module further configured to determine a standard deviation for each of the segments based on the strain values associated with the points within the segment, the processor module further configured to determine an estimate of error associated with the time to aortic valve closure based on the standard deviations, the display displaying an error indication based on the estimate of error.

15. The system of claim 11, wherein the processor module is configured to receive the data as data that corresponds to a plurality of segments, the processor module further configured to determine an average peak negative strain for each of the segments, wherein the display displays a segmented display of the plurality of segments, the display further displaying at least one of averaged time to peak negative strain values and averaged maximum contraction values corresponding to each of the segments.

16. The system of claim 11, wherein the processor module is further configured to calculate the weight value for each of the points by dividing the maximum contraction value by the time from onset to maximum contraction value to a power of four.

17. The system of claim 11, wherein the system is one of a miniaturized ultrasound imaging system, a hand carried ultrasound imaging system and a console-based ultrasound imaging system.

18. A non-transitory computer readable medium for determining a time to aortic valve closure, comprising:
  instructions to determine strain values based on data corresponding to a plurality of segments in an imaged region of a left ventricle of a heart;
  instructions to determine an average peak negative strain for each of the segments, the average peak negative strain comprising a maximum contraction value and a time from onset to maximum contraction value;
  instructions to determine a weight value for each of the average peak negative strains associated with the segments; and
  instructions to determine a time to aortic valve closure based on the weight values and the time from onset to maximum contraction values.

19. The non-transitory computer readable medium of claim 18, the instructions to weight further comprising applying relatively greater weight values to the average peak negative strains of the segments that have relatively shorter time from onset to maximum contraction values and applying relatively greater weight values to the average peak negative strains of the segments that have relatively greater maximum contraction values.

20. The non-transitory computer readable medium of claim 18, further comprising instructions to determine an estimate of error associated with the time to aortic valve closure based on the average peak negative strain and at least one preset parameter.

21. The non-transitory computer readable medium of claim 18, the instructions to determine the time to aortic valve closure further comprising computing a weighted average.

* * * * *